United States Patent [19]
Arnett et al.

[11] Patent Number: 4,959,065
[45] Date of Patent: Sep. 25, 1990

[54] BONE PLATE WITH POSITIONING MEMBER

[75] Inventors: G. William Arnett, Santa Barbara; Rick A. Buss, Camarillo; Robert A. Bruce, Ventura, all of Calif.

[73] Assignee: Techmedica, Inc., Camarillo, Calif.

[21] Appl. No.: 379,993

[22] Filed: Jul. 14, 1989

[51] Int. Cl.⁵ .............................................. A61F 5/04
[52] U.S. Cl. ....................................... 606/69; 606/71
[58] Field of Search ............. 128/92 R, 92 Y, 92 YP, 128/92 YL, 92 YR, 92 YF, 92 YE; 606/60, 61, 69, 70, 71, 72, 74, 75

[56] References Cited

U.S. PATENT DOCUMENTS

| | | | |
|---|---|---|---|
| 1,105,105 | 7/1914 | Sherman | 128/92 YP |
| 2,839,815 | 6/1958 | Reeves | 128/92 YF X |
| 4,573,458 | 3/1986 | Lower | 128/92 R |
| 4,683,878 | 8/1987 | Carter | 128/92 YP |
| 4,773,406 | 9/1988 | Spector | 128/92 YL |

FOREIGN PATENT DOCUMENTS 3538842  5/1987  Fed. Rep. of Germany .... 128/92 R

OTHER PUBLICATIONS

"McBride SMO Stainless Steel Bone Plates", Catalogue p. 87; 1943.

Primary Examiner—Robert A. Hafer
Assistant Examiner—Lynda M. Cofsky
Attorney, Agent, or Firm—Cislo & Thomas

[57] ABSTRACT

A bone plate for use in repairing bone fractures or osteotomies wherein the bone plate is provided with a positioning member which allows for ease of handling of the bone plate during the fixation process and wherein the bone plate has a upper surface having smooth or rounded surfaces which allows the upper surface of the bone plate to be juxtapositioned to soft tissue without fear of damaging the soft tissue, as by sharp edges.

20 Claims, 2 Drawing Sheets

BONE PLATE WITH POSITIONING MEMBER

BACKGROUND OF THE INVENTION

This invention relates to bone plates of the type that are used for reconstructing bones, both fractured and osteotomized, and in particular, bone plates of the type that may be found in circumstances where the bones to be reconstructed are inaccessible or are in locations that are difficult to work in, as for example, the facial area involving facial bones. The invention also has applicability to reconstruction in the hand and foot area.

While there are a number of bone plates in the prior art of various configurations and designs for allowing surgeon's use for various portions of the human anatomy, in many instances where the site of reconstruction is not easily accessible, these bone plates are difficult to handle and to position in the proper location so as to allow them to be affixed to fractured bones, which are to be fastened together, so that reconstruction can take place.

While various bone plate configurations having a plurality of holes therethrough, by which the plates may be securely fastened to adjacent bone structure, have been proposed and are to be secured in the reconstruction process, these plates are, for the most part, difficult to handle by the operating surgeon, not only because of the intrinsic smooth surfaces normally employed in the plates, but also because of the slipperiness of the materials of construction thereof. As operating surgeons are well aware, in bone reconstructive sites inaccessibility, presence of body fluids and the general overall reconstructive procedure, provide circumstances which make placement and handling of the bone fixation plates difficult, at best.

With the herein disclosed invention, many of the shortcomings of the prior art are obviated in that bone plates which are of necessity miniaturized, because of the locale in which they are to be used, are easily handled. The bone plates are provided with a variety of configurations wherein each of the configurations has at least one tab, projection or proturberance so as to make the bone plate easily handled during the bone reconstructive process and while the plate is being affixed to adjacent bone structure. Additionally, the surface of the bone plate adjacent to which skin and flesh are to overlie, is provided with a contoured or rounded configuration so that sharp edges are not presented to interfere with the reconstructive process.

The unique bone plates of the invention are peculiarly adaptable for use in facial bone reconstructive surgery, or hand or foot surgery, where the operating site is not large and where the adjacent, fractured bone fragments, to be secured together, are relatively slight in size and in configuration. With the bone plates of the herein-disclosed invention, a surgeon now finds that he may easily grasp and hold in position, during the securement process, a bone plate by a positioning member which is easily removable or positionable with respect to the remainder of the bone plate once fixation fastening members, such as screws or the like, have been set in place. After the bone plate has been secured by one or more fastening means, the positioning member is easily bent out of the way or twisted off and discarded.

A search in the U.S. Patent and Trademark Office has revealed the following patents:

| U.S. Pat. No. | Inventor | Issue Dates |
| --- | --- | --- |
| 1,105,105 | W. O'N. Sherman | July 28, 1914 |
| 2,494,229 | J. G. Collison | Jan. 10, 1950 |
| 2,947,308 | H. A. Gorman | Aug. 2, 1960 |
| 3,716,050 | Johnston | Feb. 13, 1973 |
| 4,219,015 | Steinemann | Aug. 26, 1980 |
| 4,403,607 | Woo et al | Sep. 13, 1983 |
| 4,484,570 | Sutter et al | Nov. 27, 1984 |
| 4,503,848 | Caspar et al | Mar. 12, 1985 |
| 4,524,765 | de Zbikowski | Jun. 25, 1985 |
| 4,573,458 | Lower | Mar. 4, 1986 |
| 4,683,878 | Carter | Aug. 4, 1987 |
| 4,773,406 | Spector et al | Sep. 27, 1988 |
| 4,781,183 | Casey, et al | Nov. 1, 1988 |
| 4,800,874 | David et al | Jan. 31, 1989 |

While the foregoing patents describe various bone plates and devices, none has the unique combination of features as provided for in the instant invention.

SUMMARY OF THE INVENTION

The invention is directed to a bone plate for use in bone fractures or osteotomies and comprises a flat or curved metal plate of biologically inert material such as for example titanium, or biologically resorbable material, such as any one of the plastics; as for example, polylactic acid, having one of a myriad of different configurations that would be expected to be utilized in bone fracture surgery and in particular facial reconstructive surgery. At least two spaced openings are provided in the bone plate, which are adapted to receive fasteners for securing the plate to adjacent bone structure and these fasteners may take the form of screws and the like. The bone plate has a generally flat or curved planar surface intended to be placed adjacent to the bone to which the plate is to be affixed, whereas the opposed or upper surface, which is intended to underlie surrounding tissue and the like, is provided with a contoured or rounded surface so as not to provide a sharp edge. The bone plate is also provided with a positioning member, such as a tang, protuberance, or tab portion which is removable or positionable, so as to not interfere with placement of the plate and of sufficient size to be held by either surgical appliances or the thumb and forefinger of the operating surgeon, so as to be able to steady the bone plate during the fixation process and wherein the positioning or positionable member is easily repositioned or removed, when no longer needed for the positioning and fixation process.

It is an object of the present invention to provide a bone plate for use in bone fractures or osteotomies.

It is another object of the invention to provide a unique bone plate for bone reconstructive surgery, wherein the plate has at least two spaced openings which are adapted to receive fasteners and wherein a positioning member of sufficient size, as would enable the surgen to handle the bone plate during the fixation process, is provided.

It is still another further, important object of the invention to provide a bone plate of a selected polygonal configuration wherein the plate has at least one positioning member which is removable or positionable out of the way, which makes handling of the bone plate during the fixation process practical and wherein after fixation has occurred, the positioning member may be positioned out of the way or easily removed.

It is still another, even more further, important, specific object of the invention to provide a bone plate for use in securing adjacent, fractured bone fragments, wherein the plate has rounded or contoured upper surfaces so as not to present sharp edges to surrounding tissue and wherein a bendable or removable tab or the like is provided to facilitate handling of the bone plate.

It is still another, even more further specific, important object of the invention to provide a bone plate having at least two apertures therein and wherein the surfaces of the bone plate, intended to be juxtapositioned to soft tissue, are rounded and wherein an integral tab member or the like of the same material of construction as the bone plate is provided, which tab or the like may be twisted or bent out of the plane of the bone plate, so as to facilitate removal of said tab.

It is still an even more, specific, important object of the invention to provide a bone plate having a specific configuration for joining adjacent bone structures, wherein the bone plate has at least two holes or apertures adapted to receive securing screws, in flush relationship to the upper surface of the bone plate, and wherein the upper surface thereof has rounded, lateral sides and wherein a movable or frangible positioning member is provided of sufficient size to be grasped and held by a forceps or the thumb and forefinger of the human hand.

These and other objects and features of the present invention will become apparent from the following detailed description, taken in conjunction with the accompanying drawings, wherein like numerals of reference designate like elements throughout.

DETAILED DESCRIPTION OF THE INVENTION

Figure 1:
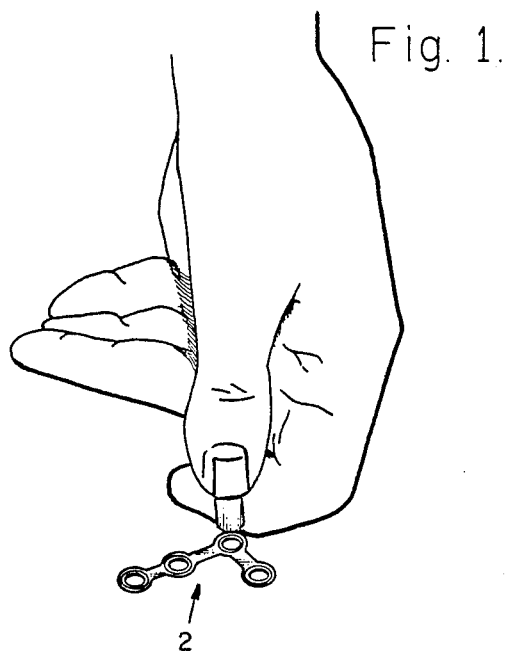
FIG. 1 is a perspective view of a simple embodiment of the invention showing a particular bone plate having a positioning portion as contemplated by the invention.
Figure 2:
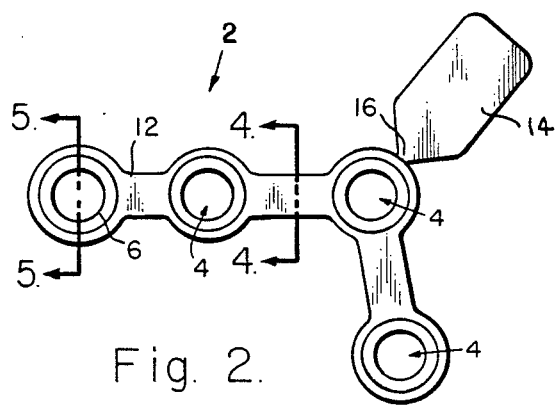
FIG. 2 is a top, plan view of the bone plate depicted in FIG. 1.
Figure 3:
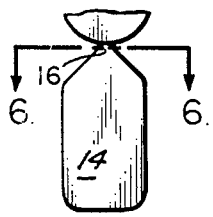
FIG. 3 is an enlarged, fragmented view of the positioning portion of the bone plate depicted in FIG. 2.

Referring to the drawings, it will be noted that the bone plate 2 of the invention, in this particular instance, has a somewhat L-shaped configuration and is of an appropriate biologically inert implant material, such as for example, medical grade titanium and has a plate thickness of about 0.024–0.036 inch although various thicknesses may be utilized, depending upon the use to which the bone plate 2 is to be put. Bone plate 2 has, as indicated earlier, a pre-selected configuration depending upon the fracture site or osteotomy wherein the bone plate is to be used. The bone plate 2 has a plurality of standard apertures or holes 4 and an angulation hole or aperture 6. It will be noted that the bone plate 2 has a flat surface 8 intended to be placed adjacent to bone or the like to which the bone plate 2 is to be secured and an upper surface 10 having rounded, lateral surfaces 12, which are intended to underlie surrounding soft tissue at the bone reconstructive site.

The bone plate 2 is provided with positioning member 14 which may be of integral construction with the remainder of bone plate 2 or may be separately affixed to a selected portion of bone plate 2. The positioning member 14 may also be of a separate material of construction which is easily malleable or bendable, or it may be of a material such as plastic which is secured to a surrounding portion of the bone plate 2, as by molding or the like, or alternately may be of a compatible metal that may be spot welded, soldered or otherwise affixed in releasable fashion to a selected portion of the bone plate.

However, in this particular instance, the positioning member 14, taking the form of a removable tab, is of a sufficient size to be grasped by the thumb and forefinger of a human hand, or at least medical instruments, and is used to position the bone plate 2 and is of the same material of construction as the remaining plate 2 which is formed during the plate formation process. The positioning member 14 has an elongated configuration with a narrowing neck portion 16, which allows for the positioning member 14 to be twisted out of the plane of the plate 2 or bent up and down so as to easily break the small neck portion 16 which is formed by stamping or other process during the formation of bone plate 2. In other instances it may be desirable to merely bend the positioning member 14 onto or towards the surface 10 of plate 2.

Figure 5:
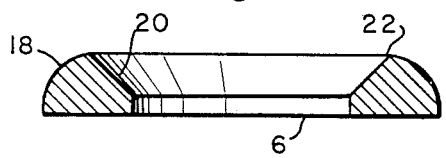
FIG. 5 is a view taken along the line 5—5 of FIG. 2.

The apertures 4 and 6 are provided with coined or beveled surfaces 18 and have an enlarged or counter bore portion 20 so as to receive a fastening screw, not shown, in almost flush relationship, so that the head of the screw does not materially or substantially extend above the surface 22 of aperture 6, as clearly seen in FIG. 5. The angulation hole or aperture 6 is slightly larger than the standard holes 4, but in all other respects has the same counter-sunk configuration and rounded edges as described for standard hole 4.

Figure 7:
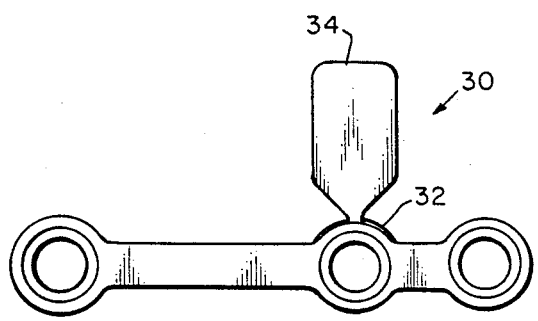
FIG. 7 is a top, plan view of another embodiment of the bone plate of the invention.
Figure 6:
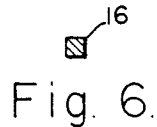
FIG. 6 is a view taken along the line 6—6 of FIG. 3.

Referring to FIG. 7, an alternative bone plate configuration is seen wherein the bone plate 30 is of elongate, linear configuration, here having a removable positioning member or tab 34 by which the bone plate 30 may be held for ease of securement and placement during the fixation process by the operating surgeon. In this instance tab 34 is of plastic being molded onto plate 30 by means of plastic strip 32 which is readily disassociated, along with the tab 34 from the plate 34.

Figure 8:
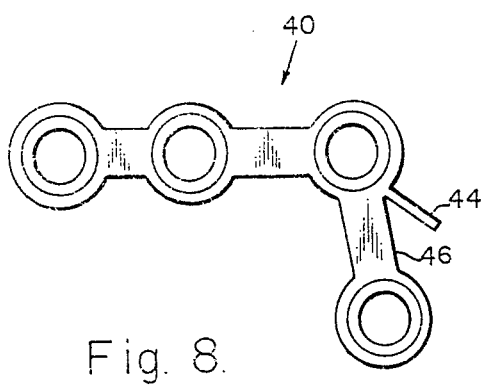
FIG. 8 is a top plan view, showing another embodiment of the invention.
Figure 9:
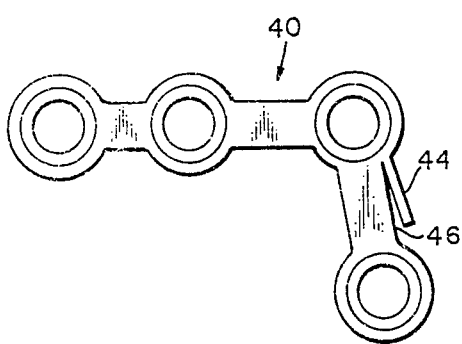
FIG. 9 is a view similar to FIG. 8, showing the positioning member bent into a non-interfering position.

FIGS. 8 and 9 illustrate another embodiment of the invention wherein the bone plate 40 has a positioning member 14, here taking the form of an extending, small-sized tab 44 which, after positioning of the bone plate 40, and fixation thereof, is bent towards the edge 46 of bone plate 40 so as to not interfere with the reconstruction process or site.

Figure 10:
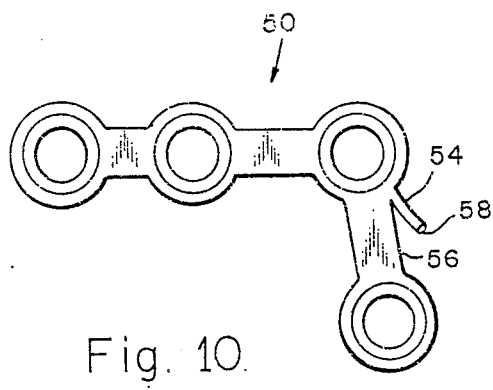
FIG. 10 is a top plan view of still another embodiment of the invention.
Figure 11:
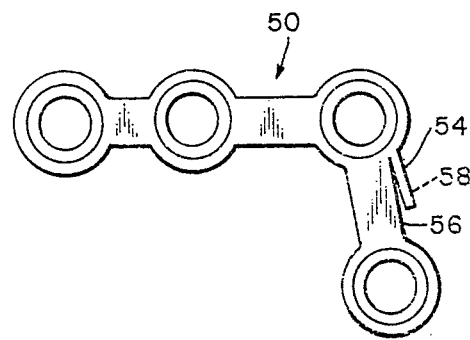
FIG. 11 is a view similar to FIG. 10 showing the positioning member moved into an out-of-the-way position.

Referring to FIGS. 10 and 11, there is illustrated a bone plate 50 having a positioning member 54 of cylindrical or tubular construction, better adapted, in some instances, for holding the bone plate 50 during the fixation process, by a surgical tool (not shown), having a head of congruent configuration to be received into the recess 58 of positioning member 54. After fixation, the positioning member is deformed or bent into the position shown in FIG. 11.

In all of the examples illustrated, the positioning member may be a tab, protuberance, tang or tube of various configurations and sizes, either removable or bendable, depending on the end result desired.

Figure 4:
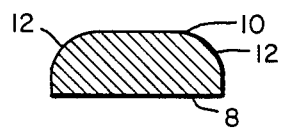
FIG. 4 is a view taken along the line 4—4 of FIG. 2.

A bone plate like that depicted in FIGS. 1-11 inclusive is ideally fabricated during a stamping operation of medically acceptable plate titanium, wherein the plate may have a thickness of about 0.0190-0.059 inch, and where, during the stamping process, the neck portion at the positioning member, where it takes the form of a removable tab, is reduced to about 0.040-0.050 inch so as to make the tab easily removable from the remainder of the bone plate. The standard hole typically is about 0.090-0.300 inch in diameter with a 45 degree countersink angle, whereas the angulation hole is about 0.98-0.300 inch in diameter. The bone plate 2 is stamped, coined or otherwise formed to have a radius in the upper surface of about 0.020-0.040 inch. The width of the bone plate, as for example shown in FIG. 4, is ideally within the range of 0.076-0.300 inch in width.

The foregoing configurations and dimensions, of course, are not absolute in that factors depending upon the ultimate configuration of the bone plate, the area of its intended use, and indeed the extent or size thereof, dictate different thicknesses, widths and other dimensions. It is only important that one or more positioning members be used, by which the bone plate may be easily positioned and affixed in the bone reconstruction process. Of importance, of course, is the fact that the positioning member taking the form of a tab, tang, or protuberance, must be easily positioned out of the way or removed once the bone plate has been at least partially secured.

While the positioning member of the bone plate of the invention has been described as being of integral construction and of the same material of construction as the remainder of the plate, those of ordinary skill in the art will of course recognize that separate or non-integral positioning members may be fashioned and secured to the bone plate by a variety of means, for ease of removal, to serve the same end function as that previously described hereinbefore. Furthermore, the bone plate may be of variable malleability construction.

Various modifications and changes to the hereindescribed invention will become obvious to those of ordinary skill in the art. For example, the particular size and configuration of the bone plate, the number of apertures used for fastening, the thicknesses and dimensions of the bone plate, are all matters which those of ordinary skill in the art will recognize and all such alterations and modifications are intended to be covered by the appended claims.

We claim:

1. A bone plate for use in bone fractures comprising the combination of:
    a generally planar plate of inert material having at least two spaced openings adapted to receive fasteners for securing said plate, said plate having a generally flat surface adapted to be placed adjacent to the bone to which said plate is to be affixed and the opposed surface thereof being generally flat with rounded edges, said plate having a readily removable positioning member which is of sufficient size to manipulate and ready said bone plate for fixation, said positioning member being adapted for quick and easy separation from said bone plate after fixation of said bone plate and intended to be removed after fixation, and said positioning member not having any of said spaced openings therein.

2. The bone plate in accordance with claim 1 wherein said at least two spaced openings are counter-sunk to receive fastening means in substantially flush relationship thereto.

3. The bone plate in accordance to claim 1 wherein said positioning member is large enough to be held by the thumb and forefinger of the human hand, or by a standard medical forcep or similar grasping instrument.

4. A bone plate for use in bone fractures comprising the combination of:
    a generally flat or curved plate of inert material having at least two spaced openings adapted to receive fasteners for securing said plate, said plate having a generally planar surface adapted to be placed adjacent to the bone to which said plate is to be affixed and the opposed surface thereof being planar with rounded edges, said plate having a positioning member which is of sufficient size to ready said bone plate for fixation;
    wherein said at least two spaced openings are counter-sunk to receive fastening means in substantially flush relationship thereto;
    wherein said positioning member is large enough to be held by the thumb and forefinger of the human hand, or by a standard medical forcep or similar grasping instrument; and
    wherein said positioning member is of tab-like configuration and is of integral construction with the remainder of said bone plate and a reduced neck portion is provided which permits said positioning member to be easily removed.

5. The bone plate in accordance with claim 4 wherein the material of construction is human medical grade titanium, titanium alloy, or other commonly used implant material.

6. The bone plate in accordance with claim 5 wherein said bone plate is of various polygonal configurations.

7. The bone plate in accordance with claim 3 wherein said positioning member comprises a different material of construction than the remainder of said bone plate.

8. The bone plate in accordance with claim 7 wherein said positioning member is affixed by malleable material.

9. The bone plate in accordance with claim 7 wherein said positioning member is removable and plastic, and is molded in removable relationship to said bone plate.

10. The bone plate in accordance with claim 6 wherein said plate is L-shaped and said removable positioning member is located at the foot of the L.

11. A bone plate for use in bone fractures comprising the combination of:
    a generally planar plate of inert material having at least two spaced openings adapted to receive fasteners for securing said plate, said plate having a generally flat surface adapted to be placed adjacent to the bone to which said plate is to be affixed and the opposite surface thereof being generally flat with rounded edges, said plate having a slender, malleable, prong-like positioning member which is of sufficient size to manipulate and ready said bone plate for fixation, said positioning member being adapted to be bent from a first position wherein said positioning member projects away from said bone plate to a second position wherein said positioning member is aligned closely adjacent said bone plate, wherein said positioning member is positionable with respect to said plate and after fixation of said bone plate is intended to be positioned in said second position.

12. The bone plate in accordance with claim 11 wherein said positioning member comprises a tubular end portion having a recess therein to receive a congruently shaped end of a surgical tool used to manipulate said bone plate.

13. A bone plate for use in bone fractures or osteotomies comprising:
a plurality of substantially planar annular portions joined by strip segments, with no more than two such strip segments adjoining any annular portion, said annular portions and strip segments having a generally D-shaped cross section, so that a lower surface of said bone plate is flat and an upper surface of said bone plate is generally flat with rounded edges; and
a positioning tab member joined to one of said annular portions, said tab member being generally thin and flat with a narrowed down neck part adjacent said annular portion adapted for easy separation of said tab member from said annular portion;
wherein said tab member is useful in manipulating said bone plate during fixation and may be easily removed after said bone plate is affixed to bone with the insertion of fastening means through said annular portions.

14. The bone plate of claim 13 wherein each of said plurality of annular portions has a central hole surrounded on said upper surface of said plate by an annular countersunk region adapted to receive fastening means having a complementarily shaped surface abutting said countersunk region.

15. The bone plate of claim 13 wherein said annular portions, strip segments, and tab member comprise a material suitable for implantation in the human body.

16. The bone plate of claim 13 wherein said positioning tab member is of integral construction with said annular portion to which said tab member is joined.

17. The bone plate of claim 13 wherein said positioning tab member comprises a different material of construction than said annular portion to which said tab member is joined.

18. The bone plate of claim 17 wherein said positioning tab member comprises a plastic material attached in such a manner that said tab member is easily separable from said annular portion.

19. The bone plate of claim 13 wherein said positioning tab member has a narrow width and a constant cross section and is adapted to have its orientation with respect to said annular portion easily changed by finger pressure or the use of a handling tool.

20. The bone plate of claim 19 wherein said positioning tab member comprises a malleable material and is easily separable from said annular portion to which said tab member is joined, by fatigue in bending said tab member along a line adjacent said annular member.

* * * * *